United States Patent [19]

Mulder

[11] 4,421,689
[45] Dec. 20, 1983

[54] DERIVATIVES OF 1,5-DIMETHYLBICYCLO [3,2,1] OCTANE, THE PREPARATION OF THESE COMPOUNDS AND THEIR USE AS PERFUME COMPOUND

[76] Inventor: Albertus J. Mulder, Badhuisweg 3, Amsterdam, Netherlands

[21] Appl. No.: 91,098

[22] Filed: Nov. 5, 1979

[30] Foreign Application Priority Data

Nov. 15, 1978 [NL] Netherlands ................ 7811285

[51] Int. Cl.³ ............... C07D 319/04; C07D 317/10; C07C 45/00
[52] U.S. Cl. .................... 549/360; 549/269; 549/433; 568/367; 568/374; 568/391
[58] Field of Search ............ 260/340.7, 340.9 R; 568/374, 591

[56] References Cited

U.S. PATENT DOCUMENTS

| | | | |
|---|---|---|---|
| 3,235,586 | 2/1966 | Hoch | 568/374 |
| 3,417,143 | 12/1968 | Kretschmar | 568/374 |
| 3,641,160 | 2/1972 | Peus et al. | 568/391 |
| 3,943,151 | 3/1976 | Corey et al. | 568/374 |
| 4,122,093 | 10/1978 | Corey et al. | 568/374 |
| 4,211,674 | 7/1980 | Lenselink | 252/522 R |
| 4,218,348 | 8/1980 | Mulder et al. | 252/522 R |

OTHER PUBLICATIONS

Krapcho et al., Chem. Comm., 1968, pp. 1615–1616.
Kreevoy et al., Journ. Amer. Chem. Soc. 82, 3064–3066, 1960.
Chem. Abstracts 9th Collective Index, p. 36400CS.

*Primary Examiner*—Ethel G. Love
*Attorney, Agent, or Firm*—Pravel, Gambrell, Hewitt, Kirk, Kimball & Dodge

[57] ABSTRACT

Derivative compounds of 1,5-dimethylbicyclo [3,2,1] octane of the general formula

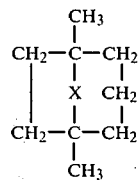

and perfume compositions containing these derivatives, wherein X represents a C=O group, a

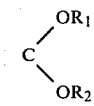

group or a

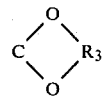

group, in which $R_1$ and $R_2$ are alkyl groups and $R_3$ is an ethylene or trimethylene group which may be substituted with one or more alkyl groups. These derivative compounds may be prepared by oxidation of 1,5-dimethylbicyclo [3,2,1] octan-8-ol or an ester thereof optionally followed by reaction with an alkanol or a 1,2- or 1,3-alkane-diol.

6 Claims, No Drawings

DERIVATIVES OF 1,5-DIMETHYLBICYCLO [3,2,1] OCTANE, THE PREPARATION OF THESE COMPOUNDS AND THEIR USE AS PERFUME COMPOUND

TECHNICAL FIELD OF THE INVENTION

The invention relates to novel derivatives of 1,5-dimethylbicyclo [3,2,1] octane, the preparation of these compounds, their use as perfume compounds and to perfume compositions, perfumed articles and materials containing said novel compounds.

PRIOR ART

One derivative of 1,5-dimethylbicyclo [3,2,1] octane, the compound of 1,5-dimethylbicyclo [3,2,1] octan-8-ol, has been disclosed in the prior art. J. K. Whitesell, R. S. Matthews and P. A. Solomon in Tetrahedron Letters No. 19, p. 1549-52 (1976) described this compound which is employed as a starting reactant to achieve the novel derivatives of the present invention.

In Chemical Communications, 1968, pp. 1615-1616, A. P. Krapcho and R. C. H. Peters describe a ketone which is wrongly indicated with the chemical name 1,5-dimethylbicyclo [3,2,1] octan-8-one and the below formula 1.

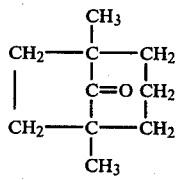

Formula 1

This ketone was obtained in small quantities as a by-product in the reaction of 2,2,6,6-tetrabromomethyl cyclohexanone of formula 2 with zinc in aqueous methanol in the presence of the mono- or di-sodium salt of ethylene diamine tetraacetic acid. The products are substantially the dispiro compound of formula 3 and the monospiro compound of formula 4.

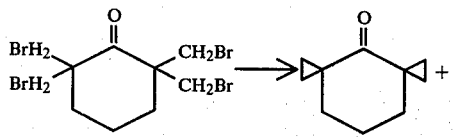

Formula 2    Formula 3

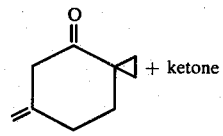

Formula 4

The ketone isolated by Krapcho and Peters had a melting point of 140°-142° C. and its NMR spectrum showed singlets at 1.05 (6H) and 1.72 (6H) and a slightly split peak at 2.22 (4H) ppm. In the infra-red spectrum of the crude reaction mixture a peak ascribed to this ketone was observed at 1740 cm$^{-1}$. The ketone reacted with Girard's reagent (trimethylaminoacetohydrazide chloride). The 2,4-dinitrophenylhydrazone of the ketone melted at 189°-190° C. and the NMR spectrum showed a pair of singlets at 1.04 and 1.08 (6H), one singlet at 1.76 (6H) and a broad multiplet at 2.35-2.70 (4H) ppm.

The ketone obtained by oxidation of 1,5-dimethylbicyclo [3,2,1] octan-8-ol has totally different properties. It is a liquid with a boiling point of 90°-91° C. at a pressure of 17 mm Hg. The IR spectrum shows a peak at 1745 cm$^{-1}$ which is ascribed to the C=O group and the NMR spectrum shows a singlet at 1.05 ppm (6H) and a broad split zone at 1.30-1.90 ppm (10H) with a peak at 1.70 ppm. Additionally, the ketone does not react with Girard's reagent. Finally, the 2,4-dinitrophenylhydrazone of the ketone melts at 167° C. and the NMR spectrum shows singlets at 1.17, 1.65 and 1.70 ppm. It is apparent that the ketone of Krapcho and Peters cannot be 1,5-dimethylbicyclo [3,2,1] octan-8-one of formula 1.

That the formula of the present invention is indeed that of formula 1, which was wrongfully ascribed by Krapcho and Peters to their by-product ketone, can be deduced from the following. The structure of 1,5-dimethylbicyclo [3,2,1] octan-8-ol was determined by Whitesell, Matthews and Solomon by means of $C_{13}$ NMR and a complete three-dimensional X-ray analysis of a monocrystal. Since reduction with LiAlH$_4$ of the ketone obtained by oxidation again yields 1,5-dimethylbicyclo [3,2,1] octan-8-ol, the oxidation only caused conversion of the OH-group into a keto-group and no change of the 1,5-dimethylbicyclo [3,2,1] octane skeleton. The skeleton according to the invention must therefore possess the structure represented by formula 1. This was confirmed by measurement of the $C_{13}$ NMR spectrum of the oxime prepared from the ketone and the IR and NMR spectrum of the 2,4-dinitrophenylhydrazone.

The ketone of Krapcho and Peters, which differs considerably from the ketone according to the invention, must therefore have been a different compound. It appears quite possible that this compound has structure 6

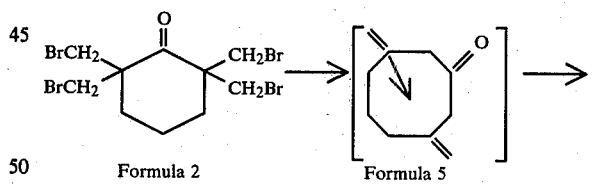

Formula 2    Formula 5

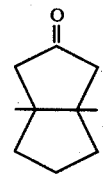

Formula 6 and is formed by rearrangement of the unstable dimethylene compound of formula 5 which is formed as intermediate. The NMR peak at 2.22 ppm (4H) points to the pressure of protons next to the C=O group and such protons are not present in formula 1. But in formula 6, protons are located next to the C=O group, which may explain the NMR peak at 2.22 ppm (4H).

SUMMARY OF THE INVENTION

It was surprisingly found that novel derivatives of 1,5-dimethylbicyclo [3,2,1] octane of the general formula 7,

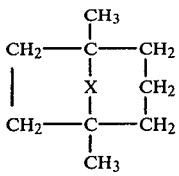

Formula 7 wherein X represents a C=O group, a

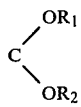

group or a

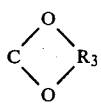

group, in which $R_1$ and $R_2$ are alkyl groups and $R_3$ is an ethylene or trimethylene group which may be substituted with one or more alkyl groups, are useful as perfume materials. The group X preferably contains not more than 10, more preferably, not more than 7 carbon atoms. Suitable examples of compounds of the general formula 7 are 1,5-dimethylbicyclo [3,2,1] octan-8-one, 1,5-dimethylbicyclo [3,2,1] octan-8-one ethylene glycol ketal, 1,5-dimethylbicyclo [3,2,1] octan-8-one propylene glycol ketal and 1,5-dimethylbicyclo [3,2,1] octan-8-one 1,3-butane diol ketal.

1,5-dimethylbicyclo [3,2,1] octan-8-one of formula 9 can be prepared according to the invention by oxidation of 1,5-dimethylbicyclo [3,2,1] octan-8-ol of formula 8.

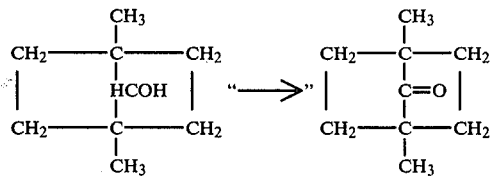

Formula 8                    Formula 9

The other above-mentioned derivatives are prepared by reacting 1,5-dimethylbicyclo [3,2,1] octan-8-one with an alkane-diol.

DETAILED DESCRIPTION

There is a growing interest in the preparation and use of synthetic perfume materials. This interest is stimulated not only by the insufficient quantity of natural perfume materials, but also by the fact that synthetic materials, unlike natural products, can be produced with a constant quality.

It has been discovered that derivatives of 1,5-dimethylbicyclo [3,2,1] octane are quite useful as perfume materials. These derivative compounds of the general formula 7 can be prepared according to the invention by oxidizing 1,5-dimethylbicyclo [3,2,1] octan-8-ol or an ester thereof with a carboxylic acid RCOOH, wherein R represents hydrogen or an optionally substituted hydrocarbon group, and if X represents a

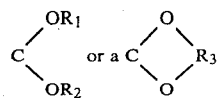

group, by reacting the ketone obtained in the oxidation with an alkanol and a 1,2 or 1,3 alkane diol respectively.

The oxidation can be carried out by means of conventional oxidants. Agents such as compounds of hexavalent chromium, $CrO_3$, $Na_2Cr_2O_7$ or $K_2Cr_2O_7$, or organic peracids, for example, performic acid, peracetic acid, peroxy trifluoroacetic acid or m-chloroperbenzoic acid perform admirably in producing the derivative compounds of the present invention. The organic peracids may be employed with a catalyst such as 2,2,6,6-tetramethylpiperidine HCl. It is also possible to use molecular oxygen in the presence of a catalyst to oxidize the 1,5-dimethylbicyclo [3,2,1] octan-8-ol.

The oxidation can be performed, for example, by heating 1,5-dimethylbicyclo [3,2,1] octan-8-ol or an ester thereof and a carboxylic acid RCOOH with $CrO_3$, $Na_2Cr_2O_7$ or $K_2Cr_2O_7$ in sulphuric acid, optionally in the presence of a solvent such as acetic acid, acetone, dichloromethane or dioxane. If a two-phase system is used, it is preferred to add a phase transfer catalyst such as tri-sec. octylmethylammonium chloride or tetrabutylammonium chloride to the reaction mixture. The reaction temperature is preferably between 15° and 100° C.

Peracids such as performic acid and peracetic acid can be prepared in situ from hydrogen peroxide and the relevant carboxylic acid. The oxidation with peracids is preferably carried out at a temperature between 30° and 95° C.

Suitable catalysts for use in the oxidation of 1,5-dimethylbicyclo [3,2,1] octan-8-ol or an ester thereof and a carboxylic acid RCOOH with molecular oxygen are platinum or palladium on carbon. The oxidation with molecular oxygen can also be carried out in the presence of a solution of manganese acetate or cobalt acetate in a carboxylic acid such as acetic acid. It is also possible to pass the compound to be oxidized in the vapor state together with oxygen or an oxygen-containing gas over a solid catalyst, for example, copper chromite or vanadium pentoxide, at a temperature of 200°–400° C.

A suitable process for the preparation of the starting material 1,5-dimethylbicyclo [3,2,1] octan-8-ol or esters thereof with a carboxylic acid RCOOH is described in the Netherlands patent application No. 78.05142. According to said patent application the relevant esters can be prepared by reacting 1,5-dimethyl-1,5-cyclooctadiene with the desired carboxylic acid. Hydrolysis of alcoholysis of the ester obtained yields 1,5-dimethylbicyclo [3,2,1] octan-8-ol.

In the oxidation employed according to the invention, the starting material is preferably 1,5-dimethylbicyclo [3,2,1] octan-8-ol or an ester thereof with formic acid, preferably, or a carboxylic acid RCOOH wherein R is an aliphatic, cycloaliphatic or aromatic hydrocarbon group with 1–7 carbon atoms. The formate can be obtained in a simple manner by heating 1,5-dimethyl- 1,5-cyclo-octadiene with excess formic acid at a temperature between 40° and 100° C. It is not necessary to isolate the formate from the reaction mixture. By addition of hydrogen peroxide followed by heating, this ester can be converted into the desired ketone which can be recovered from the reaction mixture in the usual manner.

The compounds of the general formula 7, wherein X represents a

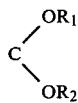

organic group or a

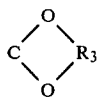

organic group, are the dialkyl acetals and the cyclic alkylene acetals (ketals) of the ketone of formula 7 respectively. These acetals can be prepared by known methods. The dialkyl acetals can be obtained by reaction of the ketone with an alkylortho formate or an aliphatic alcohol in the presence of an acid as catalyst. The cyclic alkylene acetals can be prepared by reaction of the ketone with an alkylene glycol such as ethylene glycol, propylene glycol or 1,3-butane-diol in the presence of an acid, for example, p-toluene sulphonic acid.

The compounds of the general formula 7 have such odor qualities that they are suitable to be incorporated in perfume and odor-modifying compositions. The odor of 1,5-dimethylbicyclo [3,2,1] octan-8-one may be described as coniferous and camphoric with a spicy note. Further, this substance is of importance as starting material for the preparation of the (cyclic) acetals described above. The odor of 1,5-dimethylbicyclo [3,2,1] octan-8-one ethylene glycol ketal may be described as borneol-like with a slightly earthy note. It should be noted that an earthy (geosmin-like) odor can also be highly desirable in perfumes. The odor of the corresponding propylene glycol ketal may be described as eucalyptus-like, rosemary-like and camphoric with a slightly green odor note and the odor of the corresponding 1,3-butane-diol ketal as flowery, resembling a rose, and slightly camphoric.

By the term perfume composition is meant a mixture of fragrance and optionally auxiliary components, if desired, dissolved in a suitable solvent or mixed with a powdery substrate, which is used to give a desired odor to all kinds of products and, ultimately, to the skin. Examples of such products are: soaps, detergents, washing and cleaning agents, air fresheners and room deodorants, pomanders, candles, cosmetics such as creams, ointments, toilet waters, pre and after-shave lotions, talcum powders, hair-care products, body deodorants and anti-perspirants.

Fragrance compounds and mixtures thereof which can be used for the preparation of perfume compounds are, for example, natural products such as essential oils, absolutes, resinoids, resins and concretes, and synthetic fragrance compounds such as hydrocarbons, alcohols, aldehydes, ketones, ethers, acids, esters, acetals and nitriles, including saturated and unsaturated compounds and aliphatic, carbocyclic and heterocyclic compounds.

Examples of fragrance compounds which can be used in combination with the compounds according to the invention are: geraniol, geranyl acetate, linalol, linalyl acetate, tetrahydrolinalol, citronellol, citronellyl acetate, myrcenol, myrcenyl acetate, dihydromyrcenol, dihydromyrcenyl acetate, tetrahydromyrecenol, terpineol, terpinyl acetate, nopol, nopyl acetate, betaphenylethanol, beta-phenylethyl acetate, benzyl alcohol, benzyl acetate, benzyl salicylate, benzyl benzoate, amyl salicylate, styralyl acetate, dimethylbenzylcarbinol, trichloromethyl phenylcarbinyl acetate, p-tert. butyl cylcohexyl acetate, isononyl acetate, vetiveryl acetate, vetiverol, alpha-hexylcinnamaldehyde, alpha-n-pentylcinnamaldehyde, 2-methyl-3-(p-tert.butylphenyl)-propanol, 2-methyl-3(p-isopropylphenyl)-propanol, 3-(p-tert.butylphenyl)-propanal, tricyclododecenyl acetate, tricyclododecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentanone, 2-hexyl-2-cyclopentenone, n-decanal, n-dodecanal, 9-decenol-1, phenoxyethyl-isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, heliotropin, coumarin, eugenol, vanillin, diphenyl oxide, hydroxycitronellal, ionones, methylionones, isomethylionones, irones, cis-3-hexenol and esters thereof, indanmuskfragrance compounds, tetralinmuskfragrance compounds, isochromanmuskfragrance compounds, macrocyclic ketones, macrolactone muskfragrance compounds, ethylene brassylate and aromatic nitromuskfragrance compounds.

Auxiliary components and solvents which can be used for the preparation of perfume compositions containing compounds according to the invention, are, for example, ethanol, isopropanol, diethylene glycol monoethyl ether and diethylphthalate.

The quantity of the derivative of 1,5-dimethylbicyclo [3,2,1] octane of the general formula 7 which can be used in a perfume composition or in a product to be perfumed, may vary widely and depends on the product in which the perfume material is used, the nature and the quantity of the other components of the perfume composition and the odor effect desired. In many cases, a quantity of only 0.01% by weight will have a distinctly perceptible effect on the odor of the composition, while in extract perfumes and products perfumed by means of perfume compositions, this concentration may, of course, be proportionally lower, depending on the quantity of the perfume composition used in the final product.

EXAMPLE I

A quantity of 140 ml of 98% sulphuric acid (2.6 mol) was added slowly with stirring and cooling to a solution of 143 g of Na$_2$Cr$_2$O$_7$.2H$_2$O (0.48 mol) in 160 ml of water. The temperature was maintained at 50° C. Subsequently, 3 g of tetrabutyl ammonium chloride was added and then 152 g of molten 1,5-dimethylbicyclo [3,2,1] octan-8-ol (1 mol) was added dropwise with vigorous stirring in a period of 2 hours. During this period the temperature rose to 85° C., and by controlling the speed of addition, the temperature of 85° C. was maintained. After the addition, stirring was continued vigorously for a further 30 minutes at 85° C. The reaction mixture was subsequently diluted with an equal volume of water and extracted with cyclohexane. The organic layer was washed with an aqueous solution of sodium bicarbonate and with water and dried on $Na_2SO_4$. The cyclohexane was subsequently distilled off and the residue was vacuum-distilled. The crystalline residue of the vacuum distillation was recrystallized from pentane. The compound obtained melted at 74.3° C., with a purity higher than 99% determined by gas chromatography. By means of the IR, NMR, $C_{13}$ NMR and mass spectrum it was determined that the crystalline compound was a lactone having the formula

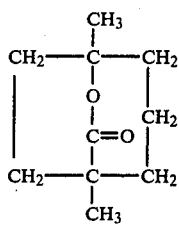

IR spectrum: 2960, 2940, 2880, 1740, 1480, 1460, 1390, 1330, 1300, 1280, 1250, 1205, 1180, 1125, 1100, 1040, 1010, 970, 940, 760, and 550 $cm^{-1}$.

NMR spectrum: 1.21, 1.32 and 1.81 ppm.

The lactone was also obtained by oxidation of 1,5-dimethylbicyclo [3,2,1] octan-8-one with peracetic acid and with m-chloroperbenzoic acid.

The distillate obtained in the vacuum distillation, after addition of 1 g of sodium in order to bind a small quantity of unconverted 1-5 dimethyl [3,2,1] octan-8-ol, was redistilled in vacuo. The yield was 140 g of 1,5-dimethyl [3,2,1] octan-8-one with a boiling point of 90°-91° C. at a pressure of 17 mm Hg. Gas chromatography revealed that the purity was higher than 99%. The IR spectrum showed peaks at 1745, 1460, 1375, 1280, 1140, and 1025 $cm^{-1}$ and the NMR spectrum showed a singlet at 1.05 ppm (6H) and a broad split zone at 1.30–1.90 ppm (10H) with a singlet at 1.70 ppm. The ketone did not react with Girard's reagent.

Derivatives

By refluxing with $NH_2OH.HCl$ in ethanol in the presence of solid NaOH, a ketone sample was converted into the oxime with a melting point after recrystallization from ethanol of 151° C. Gas chromatography revealed that the purity was higher than 99%. The IR spectrum showed peaks at 3450, 1690, 1480, 1460, 1375, 1140, 1025, 970, 940, 760 and 710 $cm^{-1}$.

By heating another ketone sample with 2,4-dinitrophenylhydrazine in diluted sulphuric acid at 50° C., it was converted into 2,4-dinitrophenylhydrazone. After recrystallization from ethanol, the melting point was 167° C. and the IR spectrum showed peaks at 3360, 3110, 1630, 1600, 1530, 1510, 1430, 1350, 1320, 1150, 1080, 1050, 940 and 750 $cm^{-1}$. The NMR spectrum showed peaks at 1.17, 1.65 and 1.70 ppm.

Reduction with $LiAlH_4$

A quantity of 7.6 g of 1,5-dimethylbicyclo [3,2,1] octan-8-one (0.05 mol) was refluxed in 50 ml of dry diethyl ether with 1.5 g of $LiAlH_4$ for 2 hours. Subsequently, 5 ml of ethyl acetate was added and the mixture was poured into a mixture of ice and 0.1N $H_2SO_4$. The ether layer was separated off and washed with water and $NaHCO_3$. After drying on $Na_2SO_4$ the ether was distilled off and the residue was recrystallized from pentane. The melting point was 43° C. The product was found to be identical with the starting material used in the oxidation, namely 1,5-dimethylbicyclo [3,2,1] octan-8-ol by tests run on IR and NMR spectrum, gas chromatography and mixed melting point.

EXAMPLE II

A quantity of 56 ml of 98% $H_2SO_4$ was added dropwise with stirring and cooling to a solution of 67 g of $CrO_3$ (0.67 mol) in 100 ml of ice water. The mixture was diluted with water to a total volume of 200 ml. The solution obtained was added with stirring to a solution of 54.6 g (0.32 mol) of the formate of 1,5-dimethylbicyclo [3,2,1] octan-8-ol and 0.5 g of tetrabutylammonium chloride in 120 ml of acetone at such a rate that the temperature of the reaction mixture was 35°-40° C. The mixture was stirred for a further 2 hours at 35° C. and subsequently, the acetone solution was separated from the bottom layer. The latter was extracted a few times with acetone and the extracts were added to the acetone solution. The mixture was washed with a saturated $K_2CO_3$ solution and subsequently dried on $K_2CO_3$. The acetone was distilled off and the residue was vacuum-distilled. The distillate was dissolved in 100 ml of pentane and refluxed for 10 minutes after the addition of 50 ml of a 25% KOH solution in methanol. The pentane solution was washed with water and dried on $Na_2SO_4$. After the pentane had been distilled off, the residue was vacuum-distilled after the addition of 1 g of sodium. A quantity of 41 g of 1,5-dimethylbicyclo [3,2,1] octan-8-one was obtained having a boiling point of 104° C. at a pressure of 22 mm Hg.

Measurement of the IR and the NMR spectrum and gas chromatography revealed that the product was identical with that obtained in Example I. The oxime and the 2,4-dinitrophenylhydrazone were also found by IR and NMR spectrum and mixed melting point tests to be identical to the corresponding compounds obtained in Example I.

EXAMPLE III

A solution of 9.7 g of $K_2Cr_2O_7$ (0.33 mol) in 200 ml of 65% $H_2SO_4$ was added with stirring to a solution of 15 g (0.1 mol) of 1,5-dimethylbicyclo [3,2,1] octan-8-ol and 1 g of tetrabutylammonium chloride in 100 ml of dichloromethane at a temperature of 40° C. for 30 minutes.

After the mixture had been stirred at 40° C. for 2 hours, the dichloromethane solution was separated off, washed with 5% $H_2SO_4$, an aqueous solution of $NaHCO_3$ and water and dried on $Na_2SO_4$. The dichloromethane was distilled off and the residue was vacuum-distilled after the addition of 0.5 g of sodium. Yield was 12 g with a boiling point at 94° C. and 20 mm Hg pressure. The product, the oxime and the 2,4-dinitrophenylhydrazone thereof were found to be identical with the corresponding compounds obtained in the Examples I and II by IR and NMR spectrum, gas chromatography and mixed melting point tests.

EXAMPLE IV

A quantity of 35 ml of 30% hydrogen peroxide was added dropwise with stirring to a solution of 18 g (0.1 mol) of the formate of 1,5-dimethylbicyclo [3,2,1] octan-8-ol in 100 ml of acetic acid at a temperature of 80°-85° C. for 30 minutes. After the reaction mixture had been stirred for a further 3 hours at a temperature of 80° C., it was diluted with water and extracted a few times with pentane. The pentane solution was washed with an aqueous NaHCO₃ solution and with water, and dried on Na₂SO₄. After the pentane had been distilled off and 0.5 g of sodium had been added, the residue was fractionally distilled in vacuum.

Yield was 11 g of 1,5-dimenthylbicyclo [3,2,1] octan-8-one with a boiling point of 90°–91° C. at a pressure of 17 mm Hg.

The product and the oxime and the 2,4-dinitrophenyl-hydrazone thereof were found to be identical with the corresponding compounds obtained in Examples I–III. From the residue obtained in the vacuum distillation, a further quantity of 1.5 g of crystalline material with a melting point of 74.1° C. was recovered. This was found to be the lactone described in Example I.

EXAMPLE V

At a rate of 10–15 liters/hour and a temperature of 80° C., oxygen was passed through a stirred suspension of 1 g of 10% platinum on carbon in a solution of 15 g of 1,5-dimethylbicyclo [3,2,1] octan-8-ol in 100 ml of dioxane. The conversion of the starting material was determined by means of gas chromatography. After oxygen had been passed through for 18 hours, 73% of the 1,5-dimethylbicyclo [3,2,1] octan-8-ol was found to have been converted and no further conversion took place. The catalyst was filtered off and 90% of the dioxane was distilled off in vacuo.

The residue was diluted with water and the mixture was extracted with pentane. The extract was washed with a diluted NaOH solution and water, and dried on Na₂SO₄. The pentane was distilled off and the residue was fractionally distilled in vacuo after the addition of 0.5 g of sodium. 8.5 g of a ketone with a boiling point of 91° C. at 18 mm Hg was obtained. Gas chromatography showed that the purity was higher than 98%. This ketone and the oxime and the 2,4-dinitrophenylhydrazone thereof were found to be identical with the corresponding compounds obtained in Examples I–IV.

The formate of 1,5-dimethylbicyclo [3,2,1] octan-8-ol was oxidized in an analogous manner, starting from a suspension of 1 g of 5% platinum on carbon in a solution of 9 g of the formate in 80 ml of dioxane. The oxidation was carried out at a temperature between 70° and 80° C. After 58% of the formate had been oxidized, no further conversion took place. After addition of a further 0.3 g of 5% platinum on carbon, a conversion of 65% was obtained. 4.1 g of the desired ketone with a purity in excess of 99% was recovered.

EXAMPLE VI

A quantity of 13.6 g of dimethyl-1,5-cyclo-octadiene (a mixture of 80% by weight of 1,5-dimethyl-1,5-cyclo-octadiene and 20% by weight of 1,6-dimethyl-1,5-cyclo-octadiene) was added at 60° C. with vigorous stirring to 50 ml of 98–100% formic acid. After the dimethyl-1,5-cyclo-octadiene had dissolved, 38 g of 30% by weight H₂O₂ was added dropwise with stirring at 60°–70° C. The mixture was heated at 90° C. for 1 hour with vigorous stirring and subsequently cooled, diluted with water and extracted with pentane. The pentane extract was washed with water, an aqueous NaHCO₃ solution and water, dried on MgSO₄ and filtered over Al₂O₃. The pentane was distilled off and the residue was fractionally distilled in vacuo by means of a Vigreu column. Yield was 7.5 g of 1,5-dimethylbicyclo [3,2,1] octan-8-one with a boiling point of 102° C. at a pressure of 24 mm Hg. The product was found to be identical with that obtained in Examples I–V by IR and NMR spectrum and gas chromatography.

EXAMPLE VII 1,5-dimethylbicyclo [3,2,1] octan-8-one ethylene glycol ketal

A mixture of 15.2 g of 1,5-dimethylbicyclo [3,2,1] octan-8-one (0.1 mol), 9 g of ethylene glycol (0.15 mol), 0.2 g of p-toluene sulphonic acid and 70 ml of toluene was refluxed in a Dean & Stark distillation head. When no further water was released, the reaction mixture was diluted with water and the layer of toluene was separated off. The latter was washed with water and an aqueous solution of NaHCO₃. After drying on Na₂SO₄, the toluene was distilled off and the residue was vacuum-distilled. The boiling point was 54° C. at a pressure of 1 mm Hg. Gas chromatography revealed that the purity of the product was higher than 99%.

IR spectrum: 2870, 1480, 1460, 1370, 1320, 1230, 1190, 1150, 1090, 1030, 970, 960, 900, 830 and 750 cm⁻¹.

NMR spectrum: 1.02, 1.72 and 3.30 ppm.

EXAMPLE VIII 1,5-dimethylbicyclo [3,2,1] octan-8-one propylene glycol ketal

A mixture of 6.1 g of 1,5-dimethylbicyclo [3,2,1] octan-8-one (0.04 mol), 9.1 g of propylene glycol (0.12 mol), 40 ml of toluene and 0.08 g of p-toluene sulphonic acid was refluxed in a Dean & Stark distillation head for 2.5 hours. The reaction mixture was poured into a saturated solution of Na₂CO₃ and the layer of toluene was separated off. After the toluene had been distilled off, the residue was vacuum-distilled. Yield was 5.9 g with a boiling point of 60°–66° C. at a pressure of 1 mm Hg.

EXAMPLE IX 1,5-dimethylbicyclo [3,2,1] octan-8-one 1,3-butane diol ketal

This compound was prepared as described in Example VIII using 1,3-butane diol instead of propylene glycol. The boiling point was 70°–75° C. at a pressure of 1 mm Hg.

The derivative compounds prepared in Examples I through IX and the processes employed to yield these compounds demonstrate the breadth of this invention. Because of the foregoing description and examples, many varying and different embodiments may be made by those skilled in the art without departing from the scope of the inventive concept herein taught or the claims appended hereto.

I claim:

1. A compound of the general formula

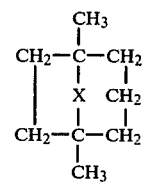

comprising a derivative of 1,5 dimethylbicyclo [3,2,1] octane wherein X is an organic group selected from the group consisting of a

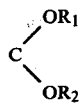

group in which $R_1$ and $R_2$ are alkyl groups or a

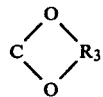

group, in which, $R_3$ is an ethylene or trimethylene group which may be substituted with one or more alkyl groups.

2. The compound of claim 1, wherein the group X contains less than 11 carbon atoms.

3. The compound of claim 1, wherein the group X contains less than 8 carbon atoms.

4. The compound of 1,5-dimethylbicyclo [3,2,1] octan-8-one ethylene glycol ketal.

5. The compound of 1,5-dimethylbicyclo [3,2,1] octan-8-one propylene glycol ketal.

6. The compound of 1,5-dimethylbicyclo [3,2,1] octan-8-one 1,3-butane-diol ketal.